(12) United States Patent
Pranzetti et al.

(10) Patent No.: US 12,245,946 B2
(45) Date of Patent: Mar. 11, 2025

(54) MODULAR REVERSE SHOULDER PROSTHESIS

(71) Applicant: Limacorporate S.p.A., San Daniele del Friuli (IT)

(72) Inventors: Antony Pranzetti, Sommacampagna (IT); Andrea Fattori, Cividale del Friuli (IT); Gabriele Vidoni, San Daniele del Friuil (IT); Michele Pressacco, Martignacco (IT)

(73) Assignee: LimaCorporate S.p.A., San Daniele del Friuli (IT)

( * ) Notice: Subject to any disclaimer, the term of this patent is extended or adjusted under 35 U.S.C. 154(b) by 0 days.

(21) Appl. No.: 18/010,370

(22) PCT Filed: Mar. 9, 2022

(86) PCT No.: PCT/EP2022/056089
§ 371 (c)(1),
(2) Date: Dec. 14, 2022

(87) PCT Pub. No.: WO2022/189532
PCT Pub. Date: Sep. 15, 2022

(65) Prior Publication Data
US 2023/0414372 A1      Dec. 28, 2023

(30) Foreign Application Priority Data
Mar. 12, 2021  (IT) .................. 102021000005858

(51) Int. Cl.
*A61F 2/40* (2006.01)
*A61B 17/16* (2006.01)
(Continued)

(52) U.S. Cl.
CPC .. *A61F 2/4003* (2013.01); *A61F 2002/30326* (2013.01); *A61F 2002/30332* (2013.01);
(Continued)

(58) Field of Classification Search
None
See application file for complete search history.

(56) References Cited

U.S. PATENT DOCUMENTS 6,790,234 B1 * 9/2004 Frankle .................. A61F 2/40
                                                  623/19.12
7,854,768 B2 * 12/2010 Wiley .................. A61F 2/4014
                                                  623/19.14

(Continued)

FOREIGN PATENT DOCUMENTS

EP   1631219 B1 *  1/2007 ............... A61F 2/34
EP   3178446 A1    6/2017
(Continued)

OTHER PUBLICATIONS

International Search Report dated May 27, 2022, issued in connection with PCT/EP2022/056089.
(Continued)

*Primary Examiner* — Ann Schillinger
(74) *Attorney, Agent, or Firm* — Akerman LLP

(57) ABSTRACT

A modular reverse shoulder prosthesis, comprising: a stem (110) comprising a tapered body (111) and a first annular housing (112); a tray (120) comprising a dome element (121) for insertion into the first annular housing (112), and further comprising a second annular housing (122); a liner (130) comprising an engaging element (131) for at least partial insertion into the dome element (121), and further comprising a joint concave element (132) configured for coupling with the second annular housing (122). The second annular housing (122) of the tray (120) comprises a raised edge (123) configured to support the joint concave element (132) and which defines an overall outline having a different development in height at least in diametrically opposite portions (123*a*; 123*b*) of the tray (120).

20 Claims, 11 Drawing Sheets

(51) Int. Cl.
*A61B 17/17* (2006.01)
*A61B 17/68* (2006.01)
*A61F 2/28* (2006.01)
*A61F 2/30* (2006.01)
*A61F 2/46* (2006.01)

(52) U.S. Cl.
CPC .............. *A61F 2002/30433* (2013.01); *A61F 2002/30604* (2013.01); *A61F 2002/4022* (2013.01); *A61F 2002/4062* (2013.01); *A61F 2310/00023* (2013.01)

(56) References Cited

U.S. PATENT DOCUMENTS

| | | | | |
|---|---|---|---|---|
| 8,337,563 | B2* | 12/2012 | Roche | A61F 2/40 623/19.12 |
| 8,888,855 | B2* | 11/2014 | Roche | A61F 2/40 623/19.12 |
| 9,216,090 | B2* | 12/2015 | Metcalfe | A61F 2/4684 |
| 9,498,344 | B2* | 11/2016 | Hodorek | A61F 2/4637 |
| 9,597,190 | B2* | 3/2017 | Chavarria | A61F 2/4014 |
| 10,335,283 | B2* | 7/2019 | Zajac | A61F 2/34 |
| 10,631,992 | B2* | 4/2020 | Hopkins | A61F 2/4081 |
| 10,898,338 | B1* | 1/2021 | Budge | A61F 2/4014 |
| 11,478,358 | B2* | 10/2022 | Miniaci | A61B 17/1684 |
| 2003/0187512 | A1* | 10/2003 | Frederick | A61F 2/4637 623/22.29 |
| 2004/0064190 | A1* | 4/2004 | Ball | A61F 2/4014 623/19.14 |
| 2006/0020344 | A1* | 1/2006 | Shultz | A61F 2/40 623/19.12 |
| 2007/0106389 | A1* | 5/2007 | Croxton | A61F 2/30942 623/22.17 |
| 2007/0173945 | A1* | 7/2007 | Wiley | A61F 2/4014 623/19.13 |
| 2012/0004733 | A1* | 1/2012 | Hodorek | A61F 2/4059 29/428 |
| 2012/0179262 | A1* | 7/2012 | Metcalfe | A61F 2/4059 623/19.14 |
| 2012/0209392 | A1* | 8/2012 | Angibaud | A61F 2/4081 623/19.11 |
| 2014/0236304 | A1 | 8/2014 | Hodorek et al. | |
| 2020/0315808 | A1* | 10/2020 | Goldberg | A61F 2/4014 |
| 2023/0137504 | A1* | 5/2023 | Gilotra | A61F 2/4081 623/19.13 |

FOREIGN PATENT DOCUMENTS

| | | | | |
|---|---|---|---|---|
| WO | WO-2012146910 | A1* | 11/2012 | A61F 2/34 |
| WO | WO-2014067961 | A1* | 5/2014 | A61B 17/56 |
| WO | 2014/096912 | A1 | 6/2014 | |
| WO | 2017/184792 | A1 | 10/2017 | |

OTHER PUBLICATIONS

Written Opinion of the International Searching Authority dated May 27, 2022, issued in connection with PCT/EP2022/056089.

* cited by examiner

MODULAR REVERSE SHOULDER PROSTHESIS

CROSS-REFERENCE TO RELATED APPLICATIONS

This application is a national phase of PCT/EP2022/056089, filed Mar. 9, 2022, and claims priority to Italian Patent Application No. 102021000005858, filed Mar. 12, 2021, the entire contents of both of which are hereby incorporated by reference.

FIELD OF APPLICATION

The present invention relates to a modular shoulder prosthesis.

The invention is particularly useful in surgeries for reverse shoulder prosthesis implantation and the following description is made with reference to this specific field of application, to simplify the exposition thereof.

In general, it is not excluded that the present invention could be applied in other types of joint prosthesis.

PRIOR ART

As it is well known, total shoulder prostheses provide a glenoidal prosthetic component and a humeral component, which articulate with each other.

In clinical practice two types of total shoulder prostheses are used.

A first type of prosthesis called "anatomical", intended to reproduce the natural anatomy of the gleno-humeral joint, provides a humeral component with a convex end that articulates on a concave end of a glenoidal component.

A second type of prosthesis called "reverse" provides instead a convex glenoidal component that articulates on a concave humeral component, after resection of the humeral head; a reverse prosthesis is preferred in critical situations of rotator cuff instability.

There are also "convertible" prostheses allowing an anatomical prosthesis to be converted into a reverse prosthesis without having to remove all the implant components, and even advantageously keeping the original bone anchorages.

In general, for a replacement of a humeral head with a prosthesis, especially in case of reverse prostheses, different elements should be provided, that allow to obtain a desired overall inclination angle of the implant, by matching several stems of the implant with several inserts. It is thereby possible to obtain better joint mobility within the limits imposed by the resection surface and the general condition of the patient's anatomy.

Document US 2014/236304 (A1) relates to a modular reverse and convertible shoulder prosthesis, that includes a distal stem, a reverse metaphysis, a reverse insert or liner that can be angled and a modular screw for coupling the reverse metaphysis with the distal stem.

Document WO 2014/067961 (A1) relates to an implantation of a convertible reverse prosthesis including a humeral stem, a reverse tray and a reverse insert or liner made of polyethylene. The reverse insert is provided in alternatives having different inclination angles, for example 7.5°, 12.5° and 17.5°.

A difficulty emerging in the prior art is due to the fact that, especially for modular reverse prostheses, the prosthesis size can involve an excessive tensioning of the surrounding tissues not only making it difficult to reduce the prosthesis at the surgical site but also leading to potential consequences in the short-medium term, among which for example a disadvantageous biomechanical configuration (suboptimal muscle lines of action, over-tensioned muscles, etc.) or bone fractures (acromial fractures due to the excessive tension). These size (and the relative consequences) are strictly connected to the position of the concave surface with respect to the humeral resection plane; specifically, the more a prosthetic design is of the "inlay" type, the more the lower point of the humeral concave joint surface is located below the resection plane; vice versa, the more a prosthetic design is of the "onlay" type, the more the lower point of the humeral concave joint surface is located above the resection plane. Especially in case of modular prostheses, the design tends to be of the onlay type since it is difficult to maintain the lower point of the humeral concave joint surface in the area below the resection plane (metaphysis), since a connection system between the several modular components that leaves little space available in said area to house the concavity of the joint surface must in fact be provided, and moreover since there are technical limits relating to the minimum thicknesses of the articulating materials.

Moreover, the onlay level can be even more evident in case of liners having their own inclination angle, unlike radially symmetrical liners; in fact, in order to ensure minimum thicknesses that are compatible with the minimum mechanical strength requirements, a slanted liner requires the lower concavity point to be risen, hence increasing the onlay level.

An excessive onlay level in a reverse modular prosthesis can therefore worsen the mobility features (rotation, extension, adduction) and in general, as described above, worsen implant performances.

Meanwhile, it is not easy to reduce the onlay level not only because of the reduced spaces in the metaphysis but also because, by bringing the joint surface of the concave liner close to the resection plane, a thinning of the liner itself, that is typically made of ultra-high molecular weight polyethylene (UHMWPE), can be observed. An excessive thinning of the liner, although supported by the metal tray, causes a reduction of the mechanical strength and thus an overall worsening of the performances of the implant, that runs the risk of damaging when subjected to loads.

A general object of the present invention is to provide to the surgeon a shoulder prosthesis that solves the drawbacks of the prior art.

A further object of the present invention is to limit or reduce the onlay level in a liner of a reverse modular prosthesis.

A further object of the present invention is to effectively allow different correction angles of a liner of a reverse modular prosthesis.

A further object of the present invention is to improve the mobility features of a shoulder prosthesis.

A further object of the present invention is to improve the mechanical strength of elements of a shoulder prosthesis, in particular of polyethylene liners.

A further object of the present invention is to have a modular prosthesis stem having improved features.

A further object of the present invention is to have a solution that can be applied to a convertible modular prosthesis, having possible anatomical prosthesis and reverse prosthesis configurations.

SUMMARY OF THE INVENTION

The solution idea underlying the present invention is to provide a modular shoulder prosthesis comprising a stem, a tray inserted into the stem and a liner coupled with the tray, forming a reverse shoulder configuration.

The tray comprises a raised edge supporting a joint concave element of the liner. The raised edge has a reduced height on the side where the angled liner is thinned, thus forming an asymmetrical tray with respect to diametrically opposite portions.

This device allows the liner to have a considerable reduction of the onlay level, but without affecting the liner minimum thicknesses and still allowing a sufficient support of the liner, especially on the full-height portions of the raised edge.

Based on this solution idea, a modular reverse shoulder prosthesis is provided, comprising: a stem comprising a tapered body and a first annular housing; a tray comprising a dome element for insertion into the first annular housing, and further comprising a second annular housing; a liner comprising an engaging element for at least partial insertion into the dome element, and further comprising a joint concave element configured for coupling with the second annular housing.

The second annular housing of the tray comprises a raised edge configured to support the joint concave element. The raised edge defines an overall outline having a different development in height at least in diametrically opposite portions of said tray.

A shoulder prosthesis system with a great modularity and versatility is thereby manufactured, that allows the implantation of different liners with different correction angles. For high correction angles too, the onlay level i.e., the distance between the bone resection plane and the lower point of the joint surface of the concave liner inserted into the tray, is reduced.

Advantageously, due to the reduction of the onlay level the mobility features (rotation, extension, adduction) and the general performances of the prosthesis are improved.

Meanwhile, advantageously, the overall outline of the tray edge, having a different or asymmetrical development in height, allows to keep sufficient thicknesses in each portion of the liner itself, improving the mechanical strength of the liner and of the overall prosthesis implant.

Further features and advantages of the invention will become apparent from the following detailed description, given by way of non-limiting example, and from the claims that are an integral part of the present description.

BRIEF DESCRIPTION OF THE DRAWINGS

In different figures, similar elements will be indicated with similar reference numbers.

The technical drawings shown in the figures are to be intended as merely illustrative, not necessarily drawn to scale or having the same scale.

DETAILED DESCRIPTION

Figure 1:
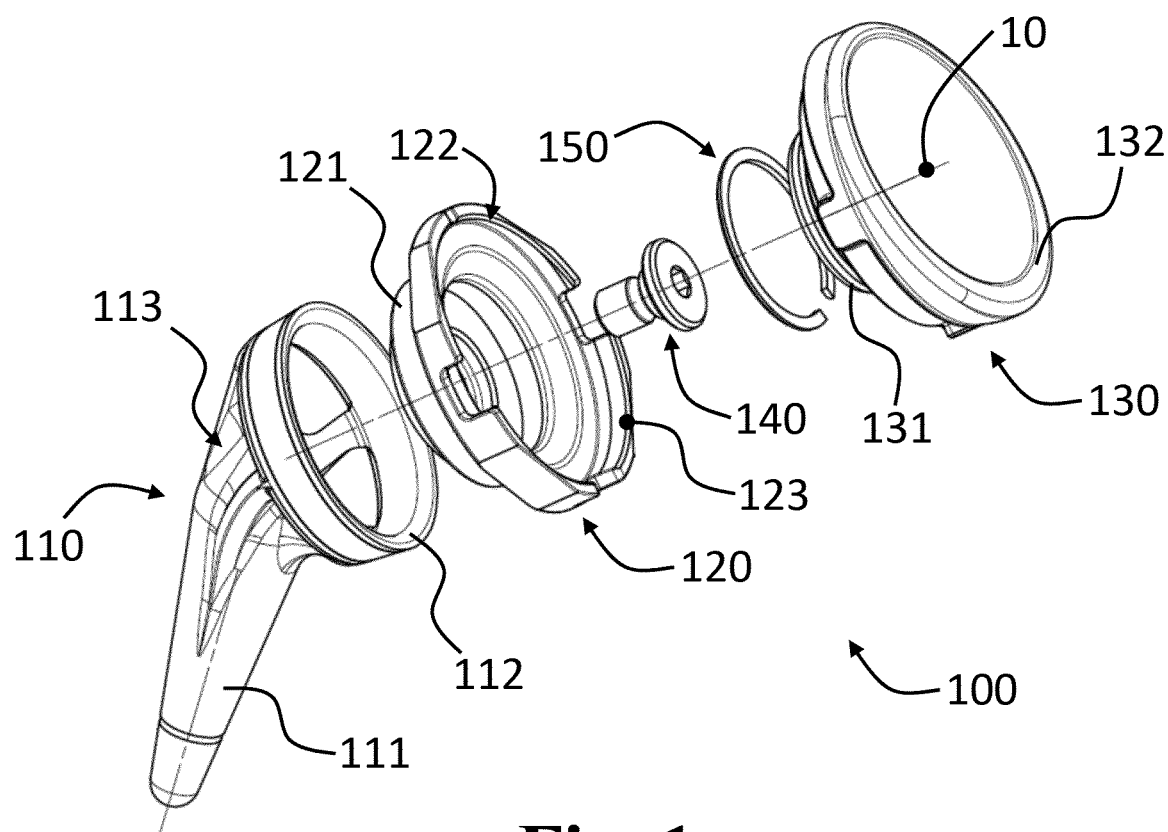
FIG. 1 shows a three-dimensional exploded view of an embodiment of a modular reverse shoulder prosthesis according to the present invention.

FIG. 1 shows a three-dimensional exploded view of an embodiment of a modular reverse shoulder prosthesis 100 according to the present invention.

The modular reverse shoulder prosthesis 100 comprises a stem 110 comprising a tapered body 111 and a first annular housing 112.

Preferably, the stem 110 further comprises a plurality of supports 113 connecting the tapered body 111 and the first annular housing 112 to each other, keeping them angled to each other. As it will be thoroughly examined below, the stem 110 falls into the category "Short Stem" of humeral prostheses that is particularly advantageous due to the reduced invasiveness and the reduced bone volume occupied by the stem, allowing the "stress shielding" phenomenon to be mitigated.

The modular reverse shoulder prosthesis 100 further comprises a tray 120 comprising a dome element 121 for insertion into the first annular housing 112 of the stem 110. The tray 120 further comprises a second annular housing 122.

The modular reverse shoulder prosthesis 100 comprises a liner 130 that includes an engaging element 131 configured for at least partial insertion into the dome element 121 of the tray 120. The liner 130 further comprises a joint concave element 132 configured for coupling with the second annular housing 122 of the tray 120. In particular, the joint concave element 132 is configured for a perimetrical coupling with the second annular housing 122 of the tray 120.

In general, the modular reverse shoulder prosthesis 100 allows a high modularity and versatility, being able to house different liners 130 having different correction angles, as it will be further described.

Moreover, the second annular housing 122 of the tray 120 comprises a raised edge 123 configured to support the joint concave element 132 of the liner 130.

The tray 120 is made of a metal material, preferably of titanium or an alloy thereof. In particular, the tapered body 111 and the first annular housing 112 are formed as a single piece in the stem 110, also including the plurality of supports 113.

The liner 130 is instead made of a plastic material, preferably polyethylene, in particular ultra-high molecular weight polyethylene (UHMWPE).

Figure 2:
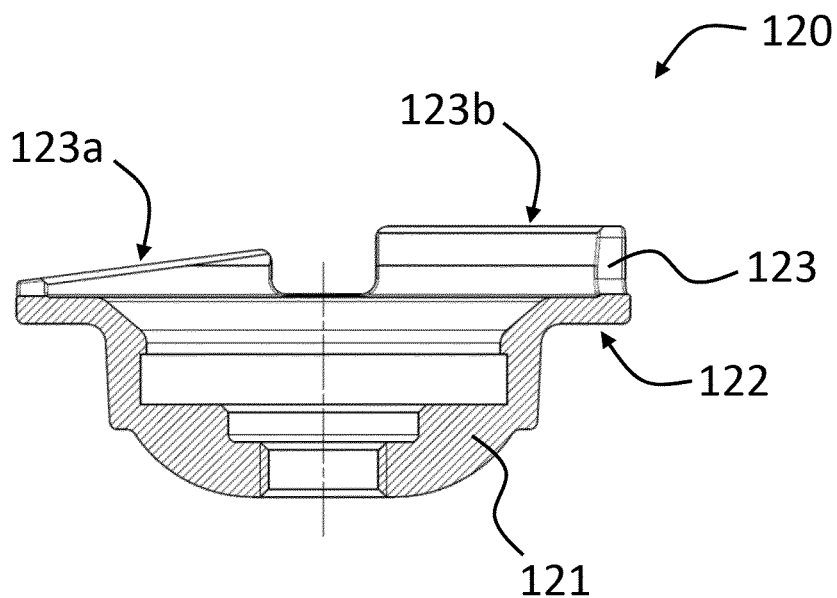
FIG. 2 shows a lateral sectional view of the tray of FIG. 1.

FIG. 2 shows a lateral sectional view of the tray 120.

As described, the tray 120 comprises the dome element 121 and the second annular housing 122. The second annular housing 122 comprises a raised edge 123, configured to support the joint concave element 132 of the liner 130 (not visible in FIG. 2).

The raised edge 123 defines an overall outline that, as can be well seen in FIG. 2, has a different development in height at least in diametrically opposite portions 123a and 123b of the tray 120.

Figure 3:
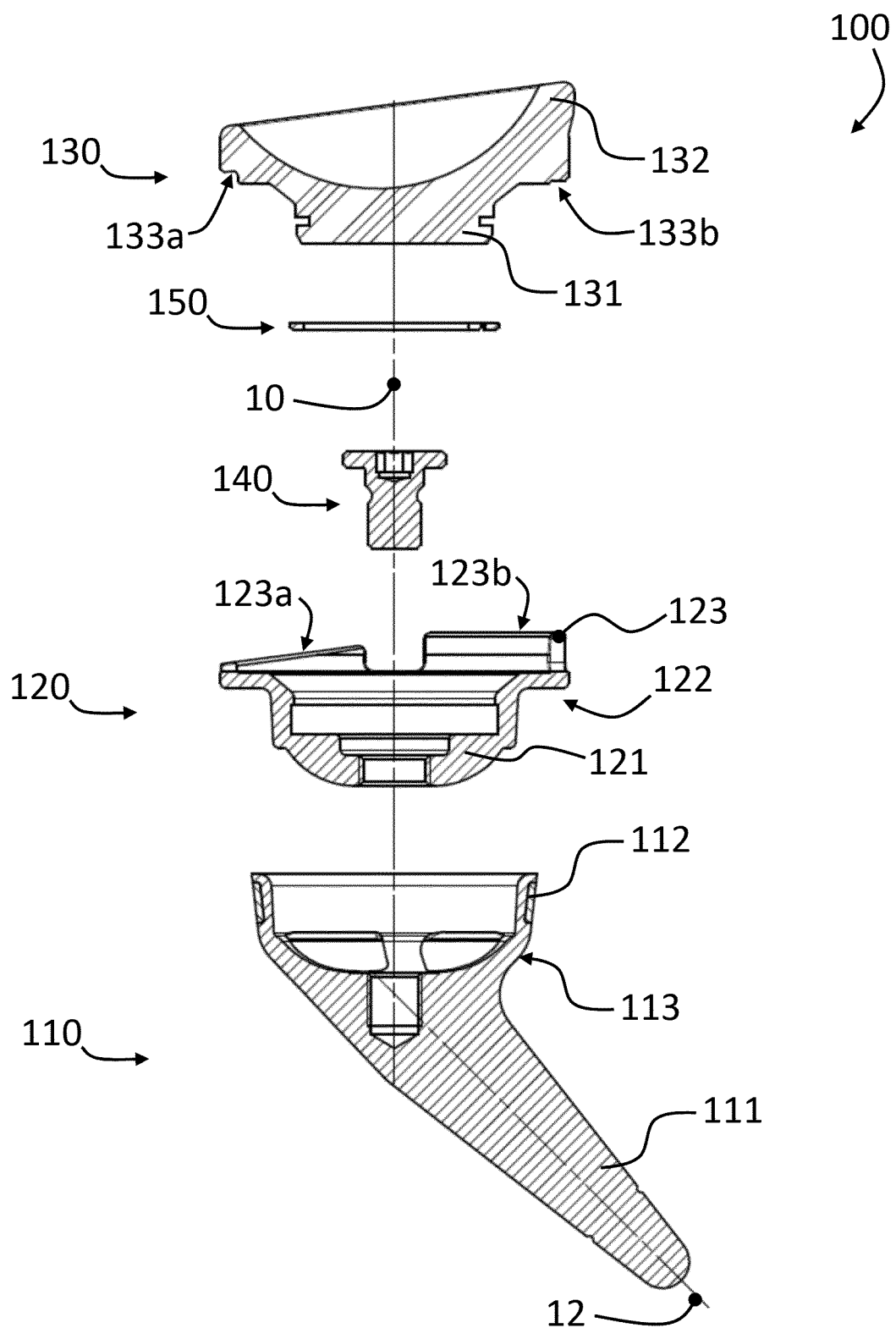
FIG. 3 shows a lateral section of an exploded view of the modular reverse shoulder prosthesis of FIG. 1.

FIG. 3 shows a lateral section of an exploded view of the modular reverse shoulder prosthesis 100, in which the already-described stem 110, tray 120 and liner 130 are represented.

Specifically, the tray 120 is assembled to the stem 110 by means of a conical coupling between the dome element 121 and the first annular housing 112, and preferably by means of a further coupling with a central safety screw 140. The liner 130 is assembled to the tray 120 by means of a snap engagement 150 acting between the engaging element 131 and an inner surface of the dome element 121. Moreover, preferably, the liner 130 is assembled to the tray 120 by means of a further interference between the engaging element 131 and an inner surface of the dome element 121.

In this view of the modular reverse shoulder prosthesis 100 it can be appreciated that the overall outline of the raised edge 123 comprises a first slanted portion 123a, configured for coupling with a respective slanted surface 133a (not visible in the figure section) of the joint concave element 132. The first portion 123a has a smaller development in height with respect to a second diametrically opposite portion 123b of the raised edge 123.

In particular, as it can be seen in FIG. 3, the dome element 121 is configured for insertion into the first annular housing 112 along an insertion axis 10, and the engaging element 131 is configured for insertion into the dome element 121 along the same insertion axis 10. In the present description, when referring to "height" or "development in height" of the raised edge of the tray 120, a dimension of the raised edge evaluated along the insertion axis 10 is to be meant.

In general, the raised edge 123 defines an overall outline having a development in height, evaluated parallelly to the insertion axis 10, that is different at least in diametrically opposite portions 123a and 123b of the tray 120.

Focusing on the first portion 123a, it substantially includes a semicircular half of the raised edge 123. In the other semicircular half of the raised edge 123, the overall outline comprises a planar portion 123b that is diametrically opposite the first portion 123a and having a greater development in height with respect thereto.

Figure 4:
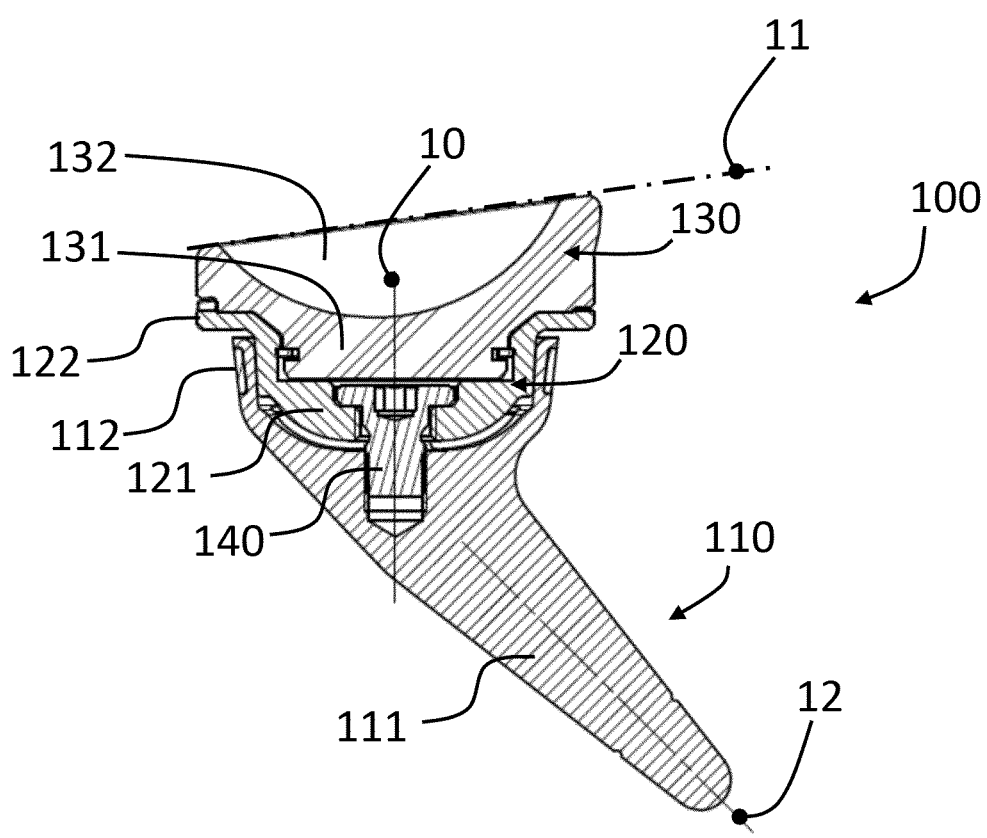
FIG. 4 shows a lateral section that is similar to FIG. 3, of an assembled view of the modular reverse shoulder prosthesis of FIG. 1.

FIG. 4 shows a lateral section that is similar to FIG. 3, of an assembled view of the modular reverse shoulder prosthesis 100.

In this view, it is appreciated that in order to form the modular structure of the prosthesis 100, the dome element 121 is configured for insertion into the first annular housing 112 along the insertion axis 10 and the engaging element 131 as well is configured for insertion into the dome element 121 along the same insertion axis 10. It is also noted that the second annular housing 122 is arranged substantially perpendicular to the insertion axis 10.

The joint concave element 132 of the liner 130 comprises an upper surface substantially lying on a correction plane 11. The correction plane 11 is slanted by a correction angle with respect to a plane that is perpendicular to the insertion axis 10. The tapered body 111 defines instead a stem primary axis 12 that is angled with respect to the insertion axis 10.

In general, the stem 110 is configured for implantation in a humeral bone end, while the liner 130 is configured to articulate with a respective glenoidal spherical element, or glenosphere, of a reverse shoulder prosthesis.

In an alternative of the shoulder prosthesis, the stem 110 is further configured to be adopted in a convertible prosthesis, and in this case the first annular housing 112 is further adapted to house prosthesis elements according to an anatomical configuration, in place of the already-described elements 120 and 130.

Figure 5:
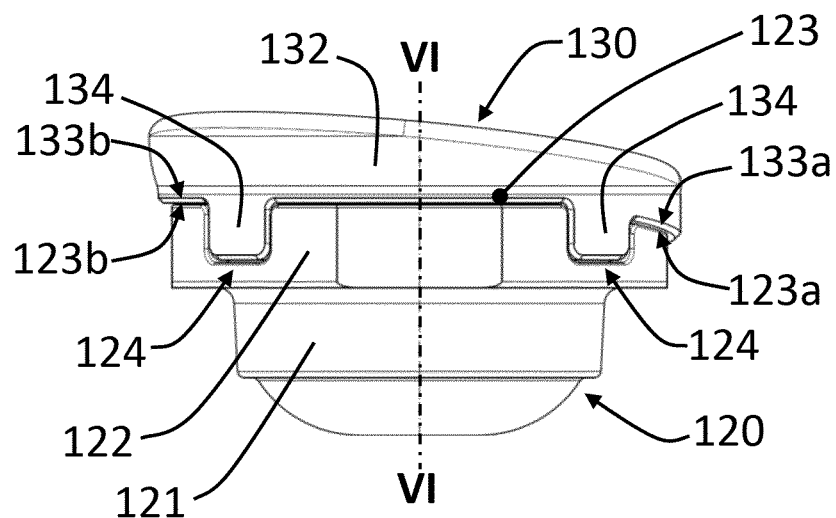
FIG. 5 shows a lateral view of a liner and tray assembly of FIG. 1.

FIG. 5 shows a lateral view of the partial prosthesis assembly comprising the liner 130 and the tray 120.

In this view it can be appreciated that the raised edge 123 comprises a plurality of cutouts 124 configured for coupling with a respective plurality of outer protrusions 134 on the joint concave element 132, that are thus adapted to block a relative rotation between the tray 120 and the liner 130.

Figure 6:
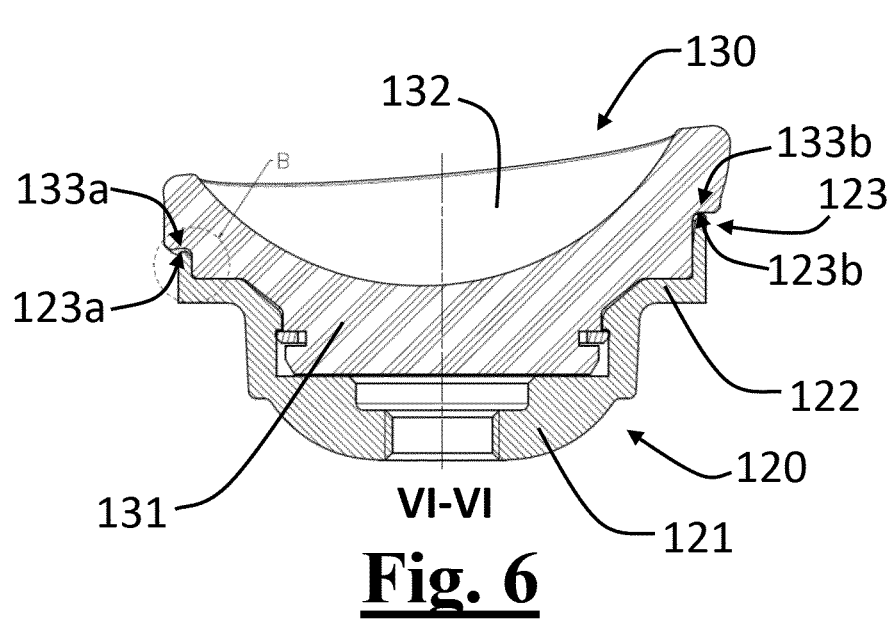
FIG. 6 shows a lateral section of FIG. 5.

FIG. 6 shows the lateral section VI-VI of the assembly of FIG. 5. As already described, the raised edge 123 defines an overall outline that, as can be seen in FIG. 6, has a development in height that is different at least in diametrically opposite portions 123a and 123b of the tray 120.

In fact, by reducing the height of the raised edge 123, on the side 123a where the liner 130 has a smaller development in height due to the provided correction angle, the tray 120 is made asymmetrical in height. This modification allows the liner 130 to have a considerable reduction of the onlay level, without however affecting the minimum thicknesses of the joint concave element 132, and still allowing a sufficient support of the liner 130 by means of the highest portion 123b of the edge 123 of the tray 120.

Figure 7:
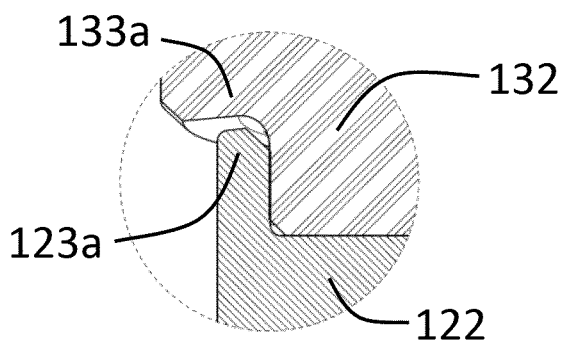
FIG. 7 shows a detail of FIG. 6.

FIG. 7 shows a detail of FIG. 6, in which the coupling between the first portion 123a of the raised edge of the annular housing 122 and the respective surface 133a of the joint concave element 132 is better viewed.

Figure 8:
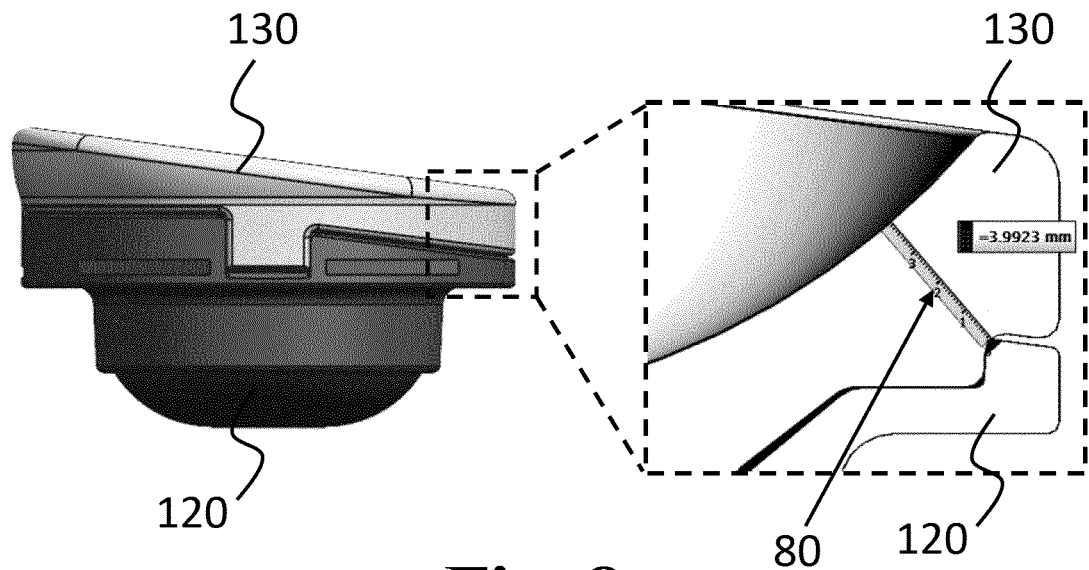
FIGS. 8 and 9 show a comparison between the thicknesses of the liner in a solution according to the present invention (FIG. 8) and according to another example (FIG. 9).
Figure 9:
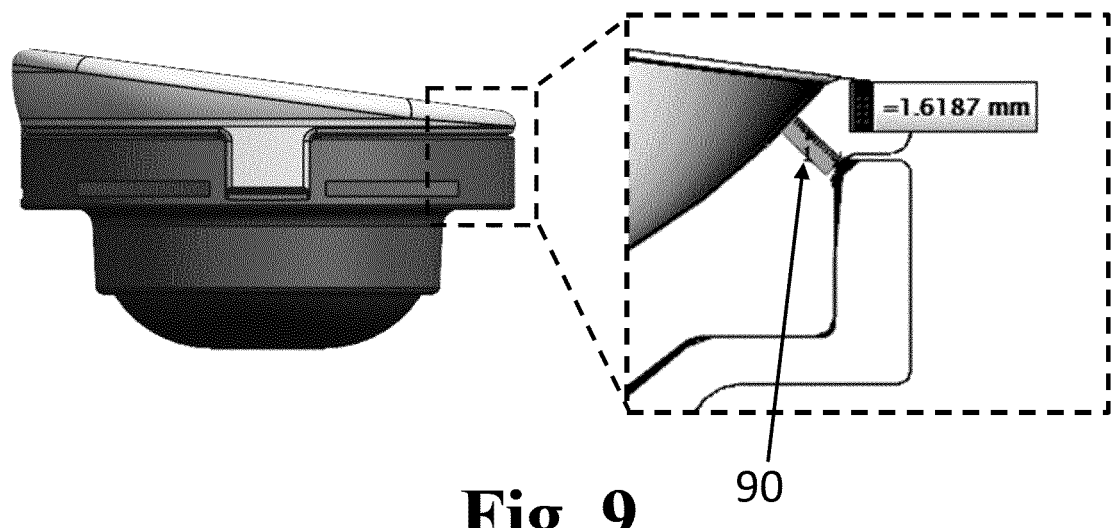

In order to clarify the effect of the present invention, FIGS. 8 and 9 show a comparison between the thicknesses of a liner in a solution according to the present invention, in FIG. 8, and according to another example, in FIG. 9. Localized magnifications in the portions identified by the dashed lines are also shown.

In FIG. 8 a tray 120 and a liner 130 are shown, in which a raised edge of the tray 120 defines an overall outline that has a different development in height at least in diametrically opposite portions, thus being asymmetrical in height. In this case, a minimum thickness 80 of the liner 130 between the concave surface and the interface with the tray 120 is by way of example 3.9923 mm.

In FIG. 9 a general tray and a general liner are shown, having a substantial diameter and size that are similar to those of the example of FIG. 8. However, in this case the raised edge of the tray defines an overall outline that has a same development in height in diametrically opposite portions, thus being symmetrical in height. In this case, the minimum thickness 90 of the liner between the concave surface and the interface with the tray is by way of example only 1.6187 mm, thus considerably smaller with respect to the minimum thickness 80 of the case of FIG. 8.

It is thus evident that in the solution of the present invention, for the same onlay level and in the presence of a same correction angle of the liners, there is no thinning of the thickness of the liner itself, to the benefit of a mechanical strength.

From another point of view, in the solution of the present invention for the same minimum thickness of the liner and thus reasonably keeping the mechanical strength properties of the liner, the onlay level can be reduced to the benefit of the prosthesis functionality and effectiveness.

Figure 11:
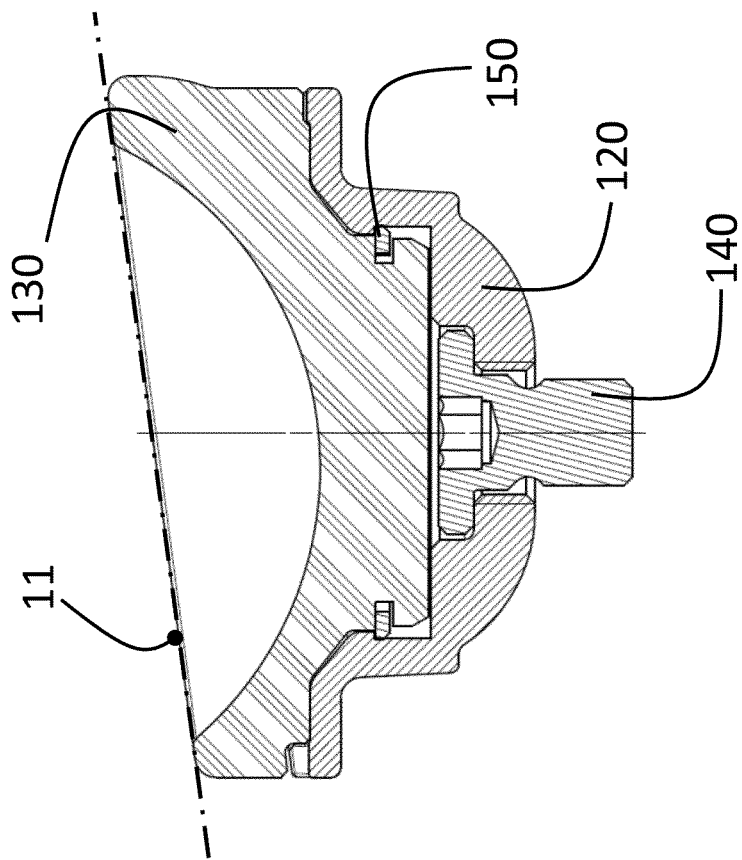
FIGS. 10 and 11 show sectional views on perpendicular planes of a liner and tray assembly of FIG. 1.
Figure 10:
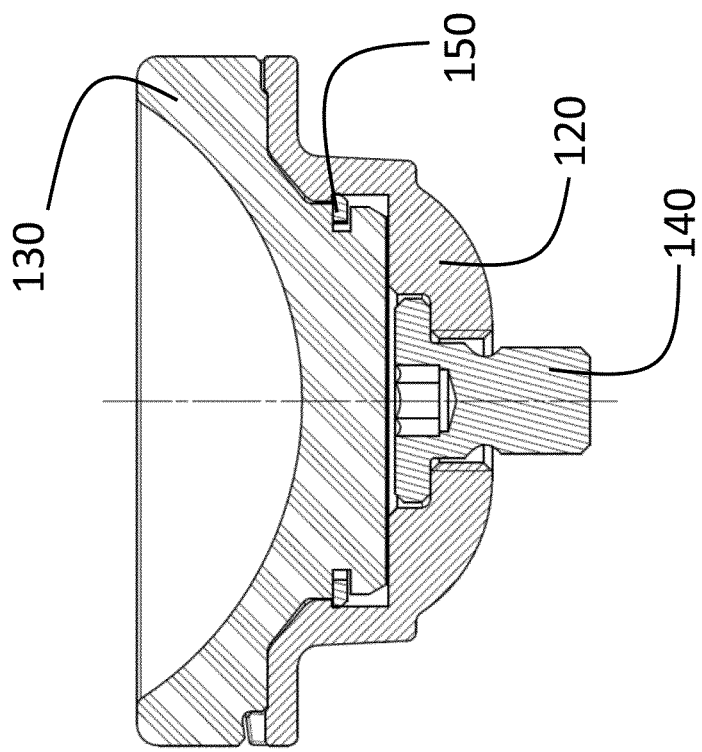

FIGS. 10 and 11 show respective sectional views on planes that are perpendicular to each other of a partial assembly composed of the already-described liner 130 and tray 120, and in addition composed of the already-described central safety screw 140 and snap engagement 150.

Figure 12:
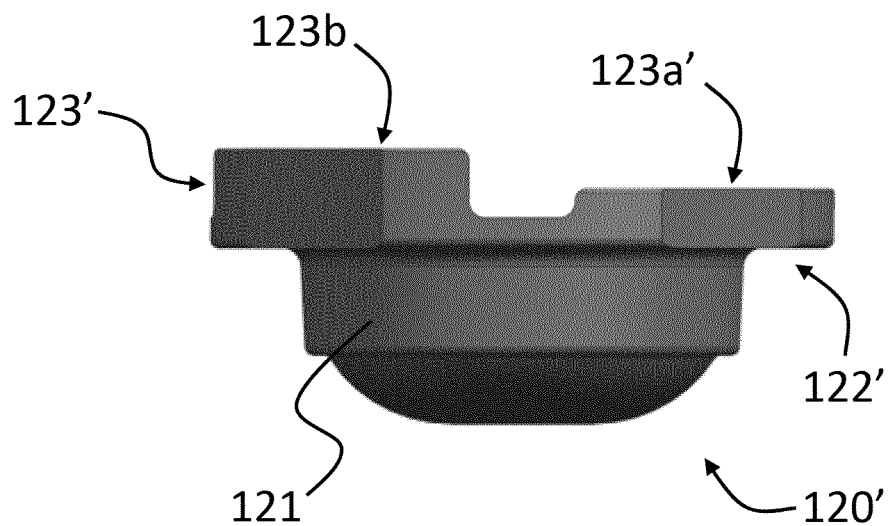
FIG. 12 shows a further embodiment of a tray for a modular reverse shoulder prosthesis according to the present invention.

FIG. 12 shows a further embodiment of a tray 120' for a modular reverse shoulder prosthesis according to the present invention.

In this alternative, the tray 120' has an annular housing 122' still comprising an asymmetrical raised edge 123', but with a planar and not slanted configuration as in the raised edge 123 of the embodiment already described above, and that complies however with the minimum thicknesses of the liner associated therewith.

In detail, the overall outline of the raised edge 123' comprises a first planar portion 123a', that still has a smaller development in height with respect to a second diametrically opposite portion 123b of the raised edge 123'. In general, the overall outline of the raised edge 123' comprises a first planar portion 123a', configured for coupling with a respective planar surface (not visible in FIG. 12) of a joint concave element.

In this alternative with the asymmetrical raised edge 123' and the first planar portion 123a', there is a greater minimum edge thickness while maintaining a same onlay level; this alternative is like a trade-off with respect to the previous exemplary embodiment and it takes thus the form of a liner with a smaller thickness with respect to the version of the angled liner 130. This trade-off is admissible as long as the minimum thicknesses required for the mechanical strength of the liner are complied with, thus limiting the correction angle of the liner.

It should also be considered that the rise of the raised edge 123' with respect to the raised edge 123, proves to be beneficial from a liner containment and stability point of view. The asymmetrical and flat raised edge 123', with respect to the asymmetrical and angled one 123, adds some material in the tray 120' where there is a coupling by interference and removes some material where there is an urging bevel for the insertion of a liner. It can thus be said that the flat version of an asymmetrical tray 120' could have more usable surface for the coupling by interference with a liner, making the assembly thereof more stable.

Figure 13:
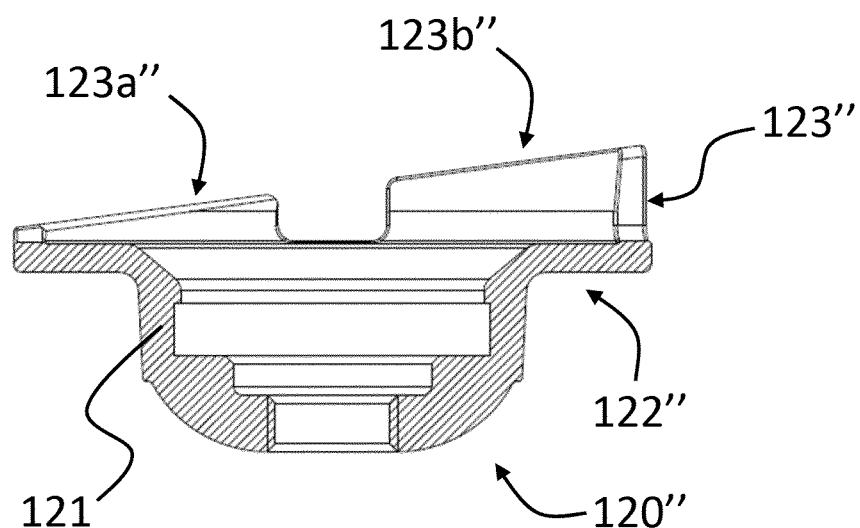
FIG. 13 shows a further embodiment of a tray for a modular reverse shoulder prosthesis according to the present invention.

FIG. 13 shows a sectional view of a further embodiment of a tray 120" for a modular reverse shoulder prosthesis according to the present invention.

In this alternative, the tray 120" has an annular housing 122" comprising an asymmetrical raised edge 123", that has a fully slanted configuration with respect to the only partially slanted configuration of the raised edge 123 of the embodiment already described above.

In detail, the overall outline of the raised edge 123" comprises a first slanted portion 123a" that has a smaller development in height with respect to a second still slanted and diametrically opposite portion 123b".

This alternative of the tray 120" with a fully slanted raised edge 123" is also admissible, as long as the minimum thicknesses required for the mechanical strength of the liner are complied with.

Figure 14:
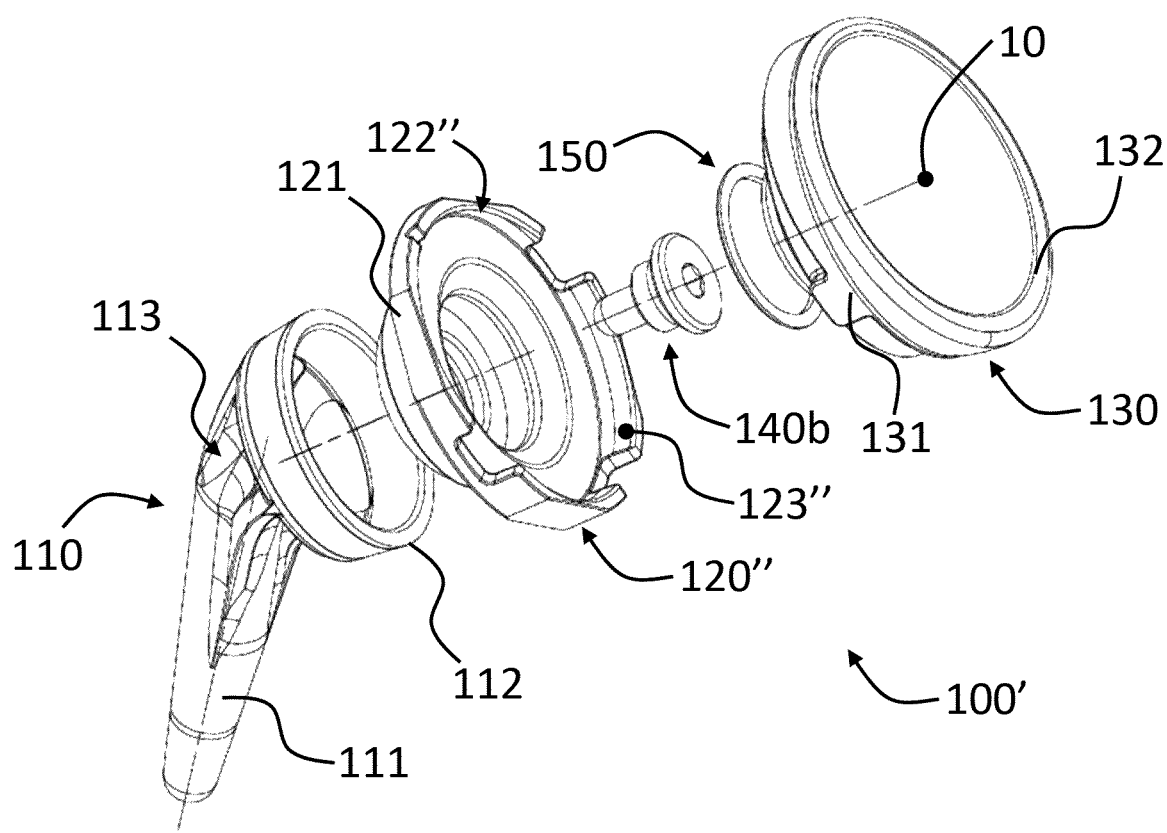
FIG. 14 shows a three-dimensional exploded view of an alternative modular reverse shoulder prosthesis according to the present invention.

FIG. 14 shows a three-dimensional exploded view of an alternative modular reverse shoulder prosthesis 100' according to the present invention.

The modular reverse shoulder prosthesis 100' comprises the already-described stem 110, tray 120" and liner 130.

In this embodiment, the tray 120" is assembled to the stem 110 by means of a conical coupling between the dome element 121 and the first annular housing 112, and by means of a further coupling with a modular pin 140b.

The modular pin 140b is preferably pre-assembled to the tray 120". With respect to the already-described screw system 140, the modular pin 140b allows the insertion of the components in the operating room to be facilitated and accelerated, and also the extraction to be accelerated in case of prosthesis revision, since it is sufficient to interpose a fork-like tool to arrange for the extraction of the tray 120" from the stem 110. Moreover, although the pin 140b offers a lower resistance to the axial extraction with respect to the screw 140, since only the conical coupling contributes to holding, it still ensures a suitable resistance to "lever-out" since in the shoulder there are basically compressive forces.

Figure 15:
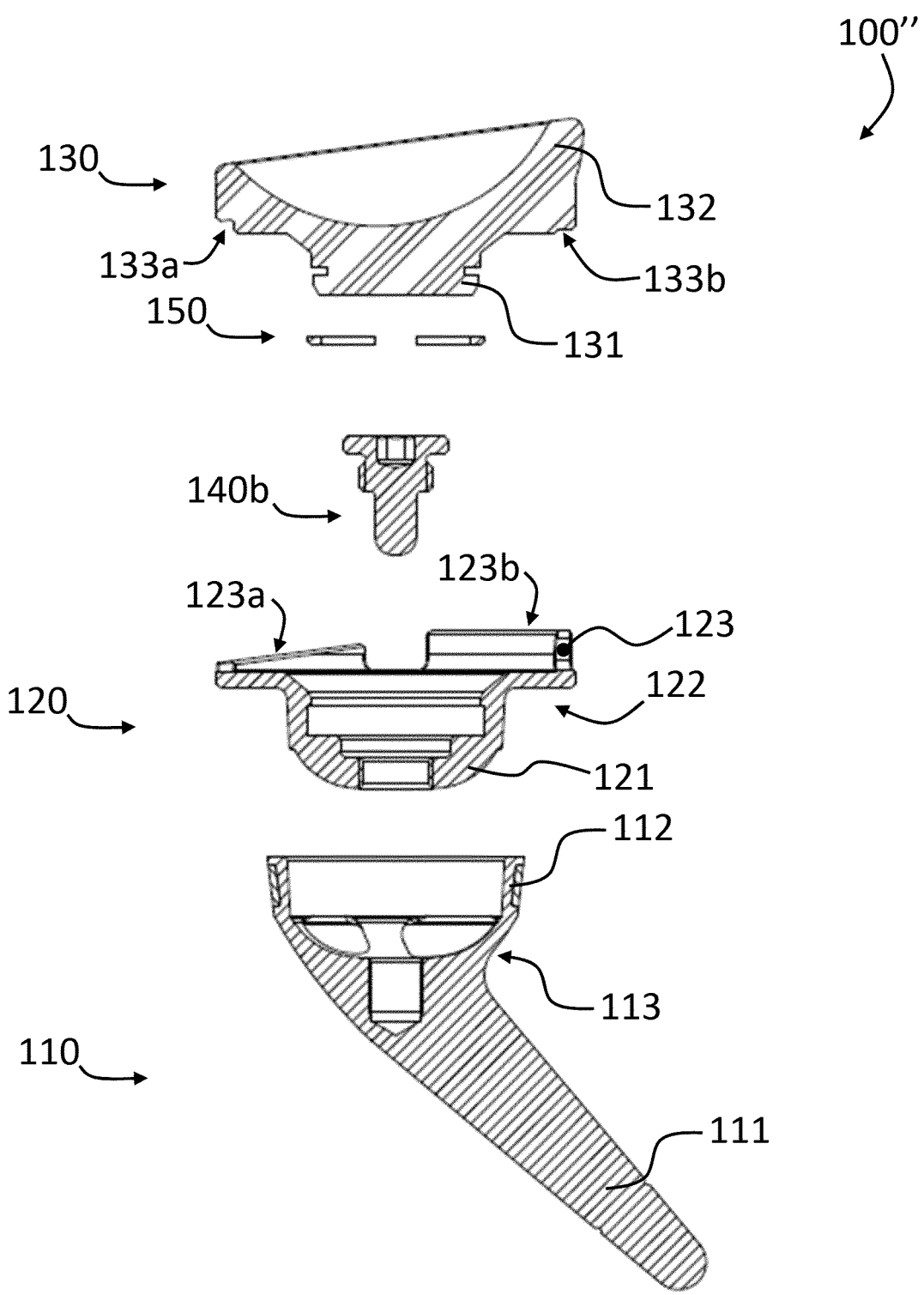
FIG. 15 shows a lateral section of an exploded view of a further alternative of a modular reverse shoulder prosthesis.

FIG. 15 shows a lateral section of an exploded view of a further alternative of a modular reverse shoulder prosthesis 100", in which the already-described stem 110, tray 120, liner 130 and modular pin 140b are represented.

In this embodiment too, preferably, the modular pin 140b is preferably pre-assembled to the tray 120.

Figure 16:
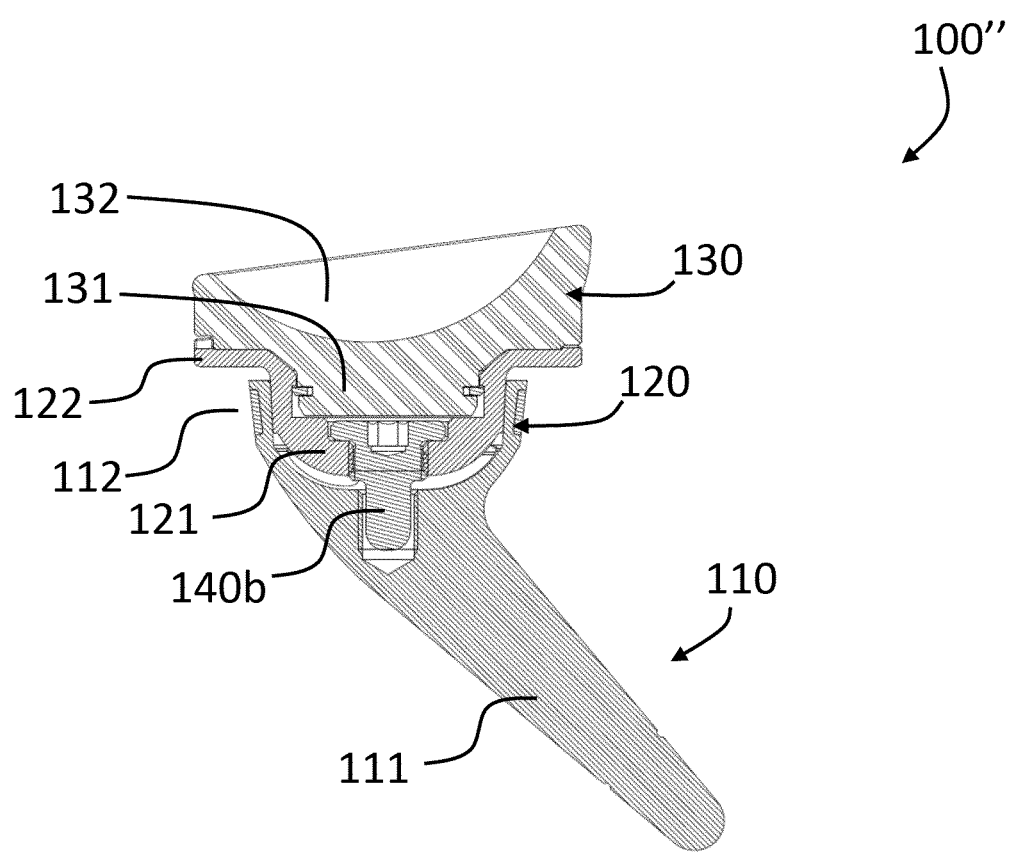
FIG. 16 shows a lateral section that is similar to FIG. 15, of an assembled view of the further alternative of a modular reverse shoulder prosthesis.

FIG. 16 shows a lateral section that is similar to FIG. 15, of an assembled view of the modular reverse shoulder prosthesis 100".

In this view, it is appreciated that in order to form the modular structure of the prosthesis 100", the dome element 121 is configured for insertion into the first annular housing 112 of the stem 110 by means of the cooperation of the pin 140b.

Figure 17:
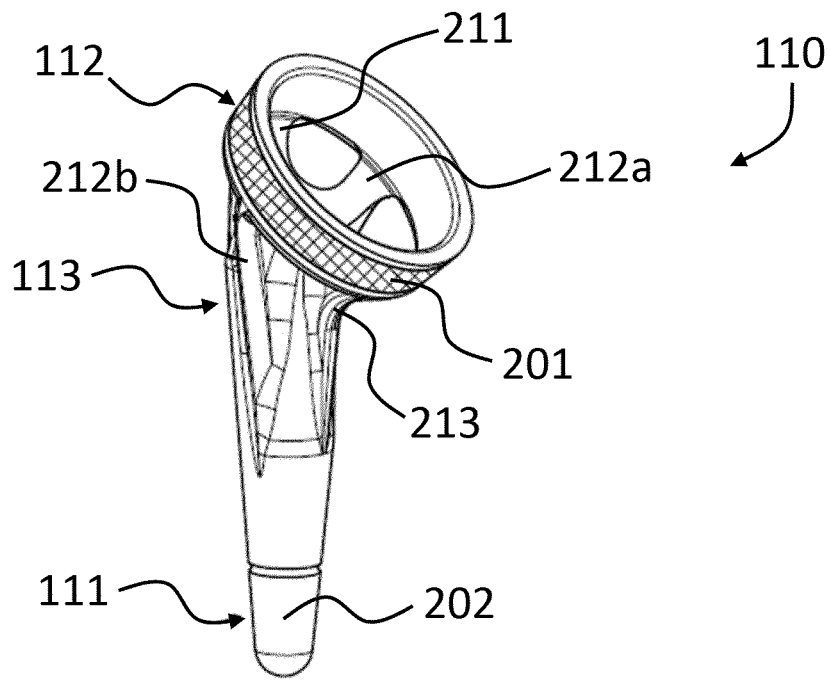
FIG. 17 shows a three-dimensional view of an embodiment of a stem for a modular reverse shoulder prosthesis according to the present invention.
Figures 18, 19:
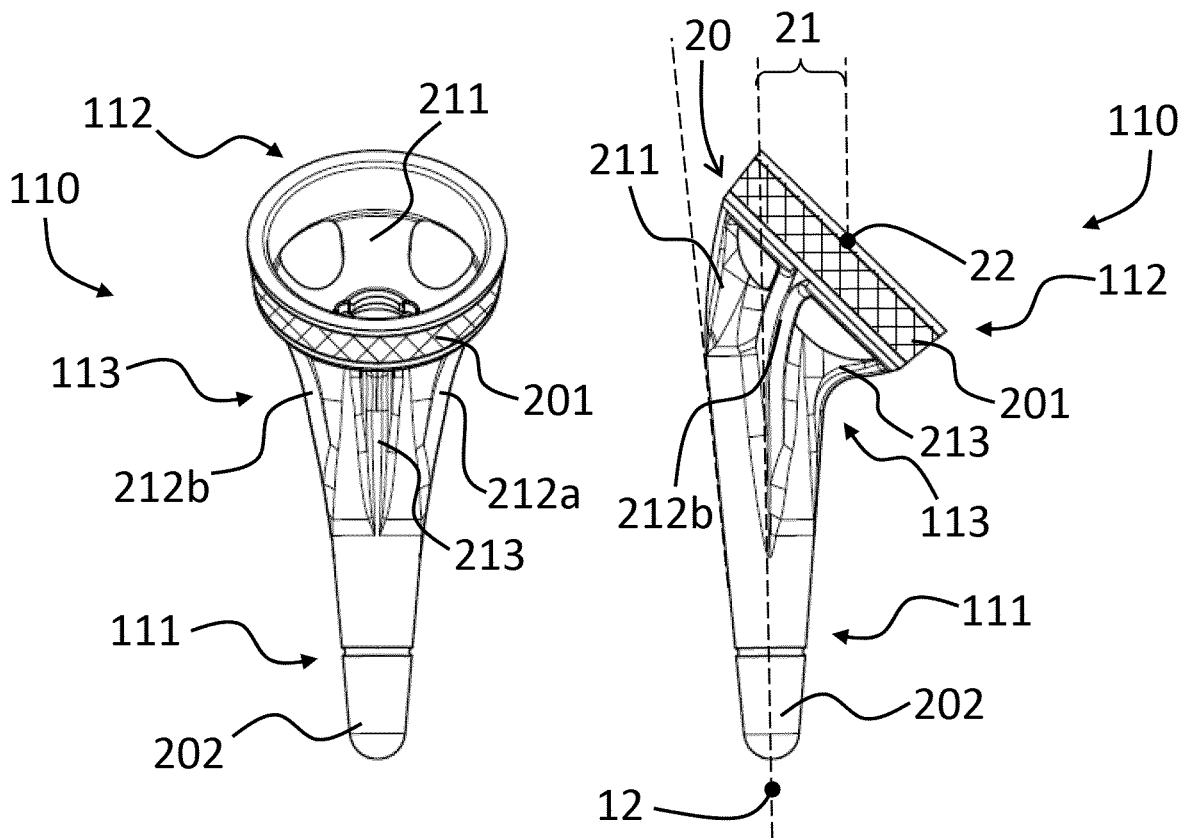
FIG. 18 shows a front view of the stem of FIG. 17.
FIG. 19 shows a lateral view of the stem of FIG. 17.

FIG. 17 shows a three-dimensional view of an embodiment of the stem 110 for a modular reverse shoulder prosthesis according to the present invention, while FIG. 18 shows a front view of the stem 110 and FIG. 19 shows a lateral view of the stem 110.

The stem 110 for a modular reverse shoulder prosthesis comprises a tapered body 111 and a first annular housing 112, configured to house other humeral components of the modular prosthesis, for example a tray 120 for the liner 130 as already described.

In the implantation of a shoulder prosthesis, the stem 110 is configured for implantation in a humeral bone end. The stem 110 is mainly configured for a modular reverse shoulder prosthesis, but it is also further configured for a convertible prosthesis, in which the first annular housing 112 is advantageously adapted to house modular anatomical prosthesis elements.

Preferably, the first annular housing 112 externally comprises a trabecular structure 201 configured to obtain a better fixation with the humeral bone. The first annular housing 112 allows the load to be transferred to the humerus, just below the resection, thus contributing to promote a better fixation of the metaphyseal type.

The stem 110 further comprises a plurality of supports 113 connecting the tapered body 111 and the first annular housing 112, keeping them angled to each other. In particular, both the tapered body 111 and the first annular housing 112 and the plurality of supports 113 are made as a single piece in the stem 110.

In general, the plurality of supports 113 are configured for a fixation and stabilisation of the prosthesis implant. In greater detail, the plurality of supports 113 define a finned portion connecting the tapered body 111 and the first annular housing 112, tapering in turn in the area connecting with the tapered body 111. In particular, the plurality of supports 113 comprise a first medial support 211, two antero-posterior supports 212a and 212b and a lateral support 213. The plurality of supports 113 are configured to provide a rotational stability to the stem 110 as well as to stabilise the bending moment.

Preferably, the conformation of the antero-posterior supports 212a and 212b is curved according to the angle between the tapered body 111 and the first annular housing 112. The curved implantation direction of the stem 110 is thereby determined, that allows to follow the medial curve of the humerus in the insertion step, better adapting to the anatomy and thus facilitating the implantation step in the operating room.

Moreover, the undercut 20 of the stem 110, due to the angle between the tapered body 111 and the first annular housing 112, allows to avoid an excessive bone removal proximally due to an insertion along the diaphisary axis of the humerus.

In an alternative, not represented, the two antero-posterior supports could be straight with respect to the stem primary axis, in order to allow an insertion of the implant in axis with the diaphisis in a more intuitive and reproducible manner.

Advantageously, the gap created between the plurality of supports 113 allows a greater lateral area of the supports 211, 212a, 212b and 213 to be exposed to the bone, improving the implant bending and torsional stability. Moreover, advantageously, the gap created between the plurality of supports 113 reduces the weight and volume of the overall implant, and considerably decreases the amount of bone to be removed for the implantation; this reduces in turn the filling coefficient (given by the ratio between the volume of bone removed from the prosthesis and the volume of bone without the prosthesis) resulting in a minor invasiveness and a minor "stress-shielding" risk. Finally, the gap created between the plurality of supports 113 allows the distal part of the prosthesis to be accessed in case of a revision intervention.

The distal portion of the stem 110, at the tapered body 111, has a substantially conical or frustoconical conformation with a circular section, that provides an additional stability to the implant, especially in the periods immediately after the surgery in which the bone is not still integrated in the first annular housing 112.

More particularly, the substantially conical shape of the stem 110 contributes to convert axial translations into circumferential forces, thus increasing the "press-fit" of the implant.

Preferably, the tapered body 111 comprises a polished end portion 202. The polished end portion 202 in addition to facilitating the insertion of the stem 110 during the surgical procedure, also allows a local osteointegration to be avoided, thus avoiding the transfer of loads distally and the consequent reabsorption of proximal bone due to "stress-shielding", and problems in the implant revision step, in which it would be otherwise difficult to access the distal portion of the tapered body 111 to detach any adherent bone without being excessively invasive.

Finally, preferably, the stem 110 is symmetrical in order to be implanted both in right and left humeri. It has however a lateral average offset 21 between the stem primary axis 12 and a centre 22 of the first annular housing 112, configured to reproduce at best the offset anatomically existing in humeri.

It should be noted that, since the stem 110 is a modular component spaced apart from the above-described tray 120 and liner 130, it could also be used in other alternatives of shoulder prostheses, both reverse and anatomical.

Moreover, it is clear that further implementations and modifications of the present invention will be possible for the person skilled in the art, in order to meet contingent needs.

The above-described embodiments are therefore to be understood as provided for illustrative and non-limiting purposes.

What is claimed is:

1. A modular reverse shoulder prosthesis, comprising:
    a stem comprising a tapered body and a first annular housing;
    a tray comprising a dome element for insertion into said first annular housing, and further comprising a second annular housing;
    a liner comprising an engaging element for at least partial insertion into said dome element, and further comprising a joint concave element configured for coupling with said second annular housing, said joint concave element comprising a concave articulation surface;
    wherein said second annular housing of said tray comprises a raised edge configured to support said joint concave element,
    wherein said raised edge defines an overall outline having a development in height that is different at least in diametrically opposite portions of said tray, and
    wherein a relative rotation between the tray and the liner is blocked.

2. The modular reverse shoulder prosthesis according to claim 1, wherein said overall outline of said raised edge comprises a first planar portion, configured for coupling with a respective planar surface of said joint concave element, said first planar portion having a smaller development in height with respect to a second diametrically opposite portion of said raised edge.

3. The modular reverse shoulder prosthesis according to claim 1, wherein said overall outline of said raised edge comprises a first slanted portion, configured for coupling with a respective slanted surface of said joint concave element, said first slanted portion having a smaller development in height with respect to a second diametrically opposite portion of said raised edge.

4. The modular reverse shoulder prosthesis according to claim 2, wherein said first planar portion substantially includes a semicircular half of said raised edge.

5. The modular reverse shoulder prosthesis according to claim 3, wherein said overall outline of said raised edge comprises a planar portion that is diametrically opposite said first slanted portion and having a greater development in height with respect to said first slanted portion.

6. The modular reverse shoulder prosthesis according to claim 1, wherein said raised edge comprises a plurality of cutouts configured for coupling with a respective plurality of outer protrusions on said joint concave element, so as to block the relative rotation between the tray and the liner.

7. The modular reverse shoulder prosthesis according to claim 1, wherein said dome element is configured for insertion into said first annular housing along an insertion axis, and wherein said engaging element is configured for insertion into said dome element along said insertion axis, and wherein said second annular housing is arranged substantially perpendicular to said insertion axis.

8. The modular reverse shoulder prosthesis according to claim 7, wherein said joint concave element of said liner comprises an upper surface substantially lying on a correction plane, said correction plane being slanted by a correction angle with respect to a plane that is perpendicular to said insertion axis.

9. The modular reverse shoulder prosthesis according to claim 7, wherein said tapered body defines a stem primary axis that is angled with respect to said insertion axis.

10. The modular reverse shoulder prosthesis according to claim 7, wherein said raised edge defines said overall outline having a development in height, said development in height being evaluated parallelly to said insertion axis and being different at least in diametrically opposite portions of said tray.

11. The modular reverse shoulder prosthesis according to claim 1, wherein said tray is assembled to said stem by a conical coupling between said dome element and said first annular housing.

12. The modular reverse shoulder prosthesis according to claim 1, wherein said liner is assembled to said tray by a snap engagement between said engaging element and an inner surface of said dome element.

13. The modular reverse shoulder prosthesis according to claim 1, wherein said tray is made of a metal material, and wherein said liner is made of a plastic material.

14. The modular reverse shoulder prosthesis according to claim 1, wherein said stem further comprises a plurality of supports connecting said tapered body and said first annular housing, keeping them angled to each other.

15. The modular reverse shoulder prosthesis according to claim 14, wherein said plurality of supports comprise a first medial support, two antero-posterior supports and a lateral support.

16. The modular reverse shoulder prosthesis according to claim 15, wherein said antero-posterior supports have a curved conformation according to an angle between said tapered body and said first annular housing.

17. The modular reverse shoulder prosthesis according to claim 1, wherein said first annular housing externally comprises a trabecular structure.

18. The modular reverse shoulder prosthesis according to claim 1, wherein said stem is configured for implantation in a humeral bone end, and wherein said liner is configured to articulate with a respective glenoidal spherical element of a reverse shoulder prosthesis.

19. The modular reverse shoulder prosthesis according to claim 1, wherein said stem is further configured for a convertible prosthesis, said first annular housing being further adapted to house prosthesis elements according to an anatomical configuration.

20. The modular reverse shoulder prosthesis according to claim 1, wherein said tapered body has a substantially conical or frustoconical conformation with a circular section.

* * * * *